United States Patent
Garoff et al.

(10) Patent No.: US 6,365,540 B1
(45) Date of Patent: Apr. 2, 2002

(54) PRODUCT CONTAINING MAGNESIUM, HALOGEN AND ALKOXY

(75) Inventors: Thomas Garoff, Helsinki; Timo Leinonen, Tolkkinen; Sirpa Ala-Huikku, Helsinki, all of (FI)

(73) Assignee: Borealis Technology OY, Porvoo (FI)

( * ) Notice: Subject to any disclaimer, the term of this patent is extended or adjusted under 35 U.S.C. 154(b) by 0 days.

(21) Appl. No.: 09/582,273

(22) PCT Filed: Dec. 21, 1998

(86) PCT No.: PCT/FI98/01002
§ 371 Date: Aug. 11, 2000
§ 102(e) Date: Aug. 11, 2000

(87) PCT Pub. No.: WO99/33842
PCT Pub. Date: Jul. 8, 1999

(30) Foreign Application Priority Data

Dec. 23, 1997 (FI) .................................. 974621
Dec. 23, 1997 (FI) .................................. 974622

(51) Int. Cl.⁷ .................. B01J 31/00; B01J 37/00; C08F 4/02; C08F 4/60
(52) U.S. Cl. ................ 502/169; 502/171; 502/133; 502/103; 502/104
(58) Field of Search ............... 502/133, 153, 502/154, 169, 171

(56) References Cited

U.S. PATENT DOCUMENTS

| | | | |
|---|---|---|---|
| 4,220,554 A | * 9/1980 | Scata et al. | 502/133 |
| 4,451,688 A | * 5/1984 | Kuroda et al. | 502/133 |
| 4,727,051 A | 2/1988 | Breen et al. | 502/171 |

FOREIGN PATENT DOCUMENTS

| | | |
|---|---|---|
| EP | A3271843 | 6/1988 |
| EP | A297076 | 12/1988 |
| EP | A1526941 | 2/1993 |
| WO | A1-9105608 | 5/1991 |
| WO | WO 92/16533 | 10/1992 |

OTHER PUBLICATIONS

Rompps Chemie–Lexikon, 7th Ed. Franckh'sche Verlagshandlung, W. Keller & Co., Stuttgart, 1973, Band 3, p. 1831.
Principles of Organometallic Chemistry, Methuen & Co. London, 1971, pp. 60–61, Coates, G. E. et al.

* cited by examiner

Primary Examiner—Mark L. Bell
Assistant Examiner—J. Pasterczyk
(74) Attorney, Agent, or Firm—Birch, Stewart, Kolasch & Birch, LLP

(57) ABSTRACT

The invention relates to a complex product containing magnesium, halogen and alkoxy, which has the following composition:

$$Mg_pX_q(OR)_{2p-q}$$

wherein X is a halogen, R is an alkyl group having from 1 to 20 carbon atoms, p is from 2 to 20 and q is from 1 to (2p−1). More specifically the complex product is a complex of the formula $$MgCl_2 \cdot [Mg(OR)_2]_2$$

wherein R is an alkyl having from 4 to 10 carbon atoms. The complex is soluble in non-polar solvents and can be used in the preparation of transition metal components of Ziegler-Natta catalyst systems.

55 Claims, 11 Drawing Sheets

The principles for preparing a solution containing a complex according to the invention

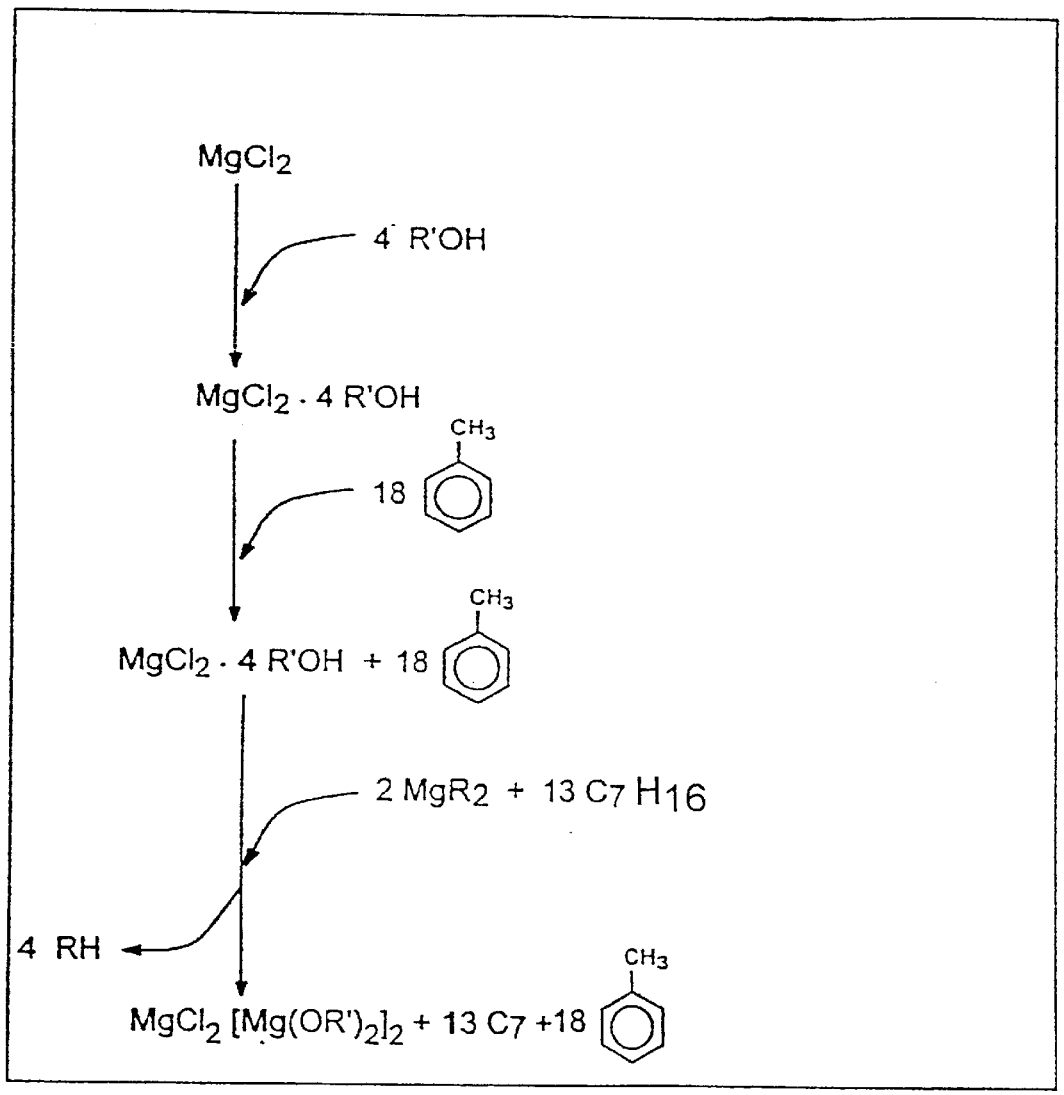
Figure 1. The principles for preparing a solution containing a complex according to the invention

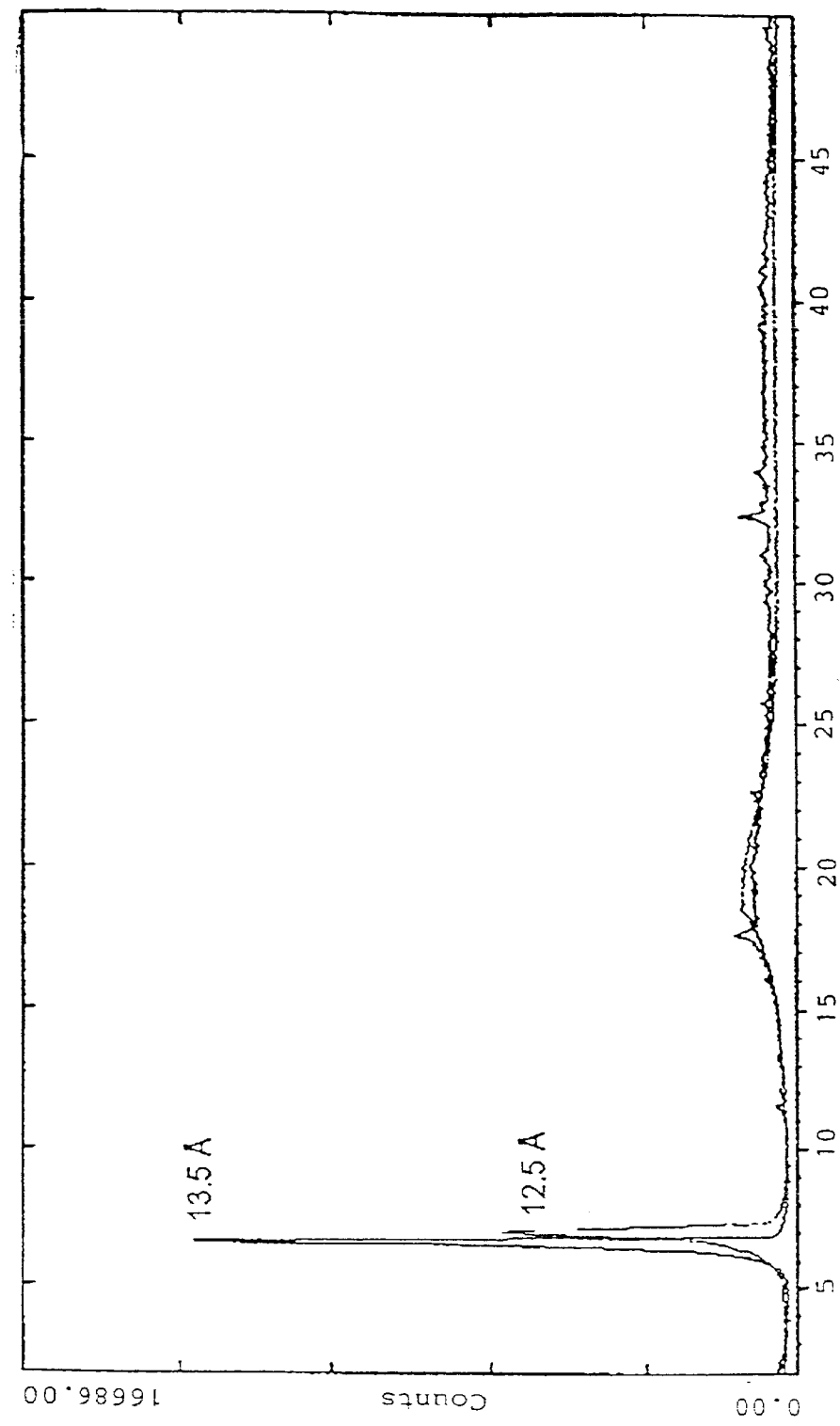
Figure 2. The X-ray diffraction patterns of $Mg(OR)_2$ (12.5 Å) and for the $MgCl_2 \cdot 2ROH$ (13.5 Å)

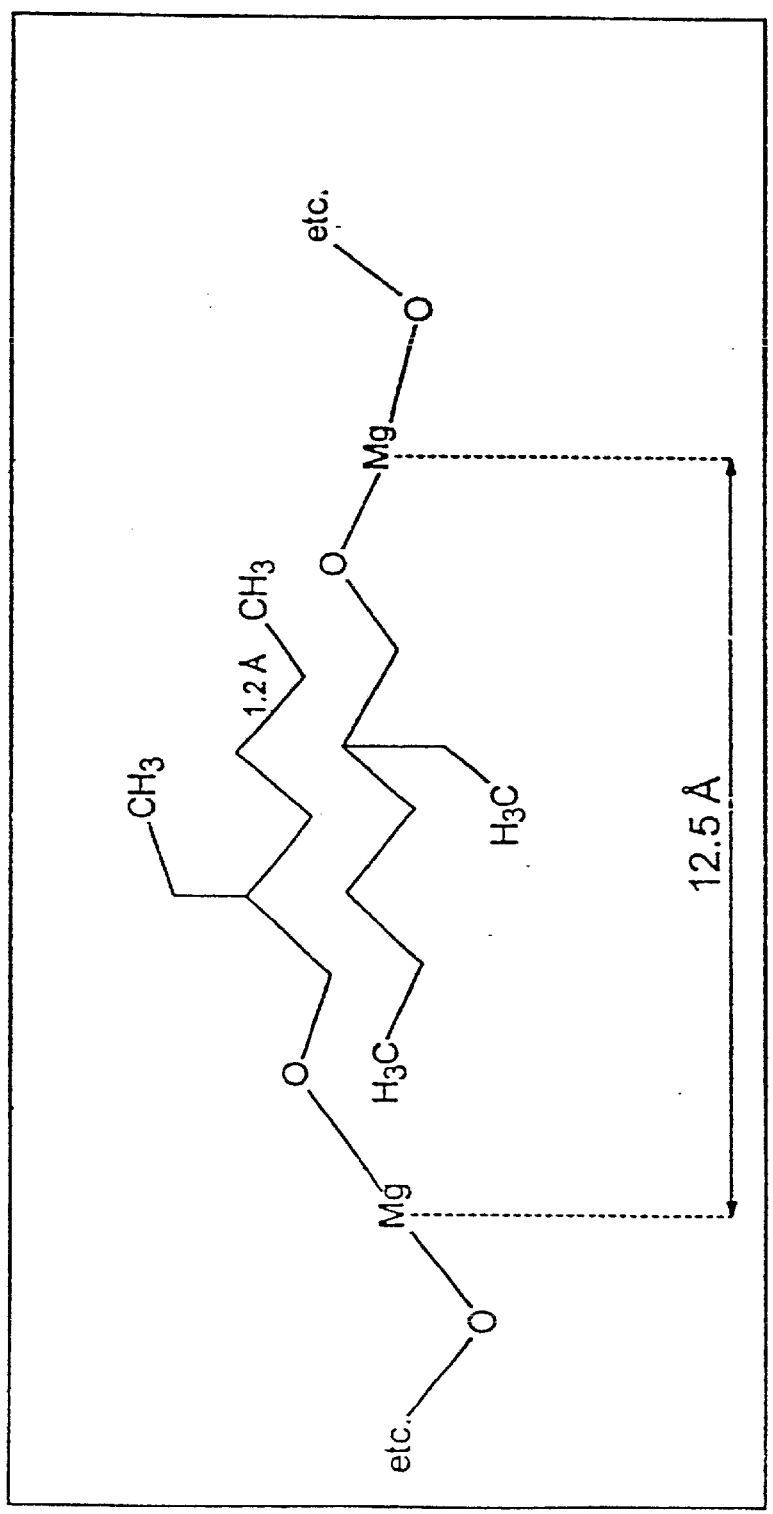
Figure 3. Most probable complexation of Mg(OR)2 giving a 12.5 Å distance between Mg.

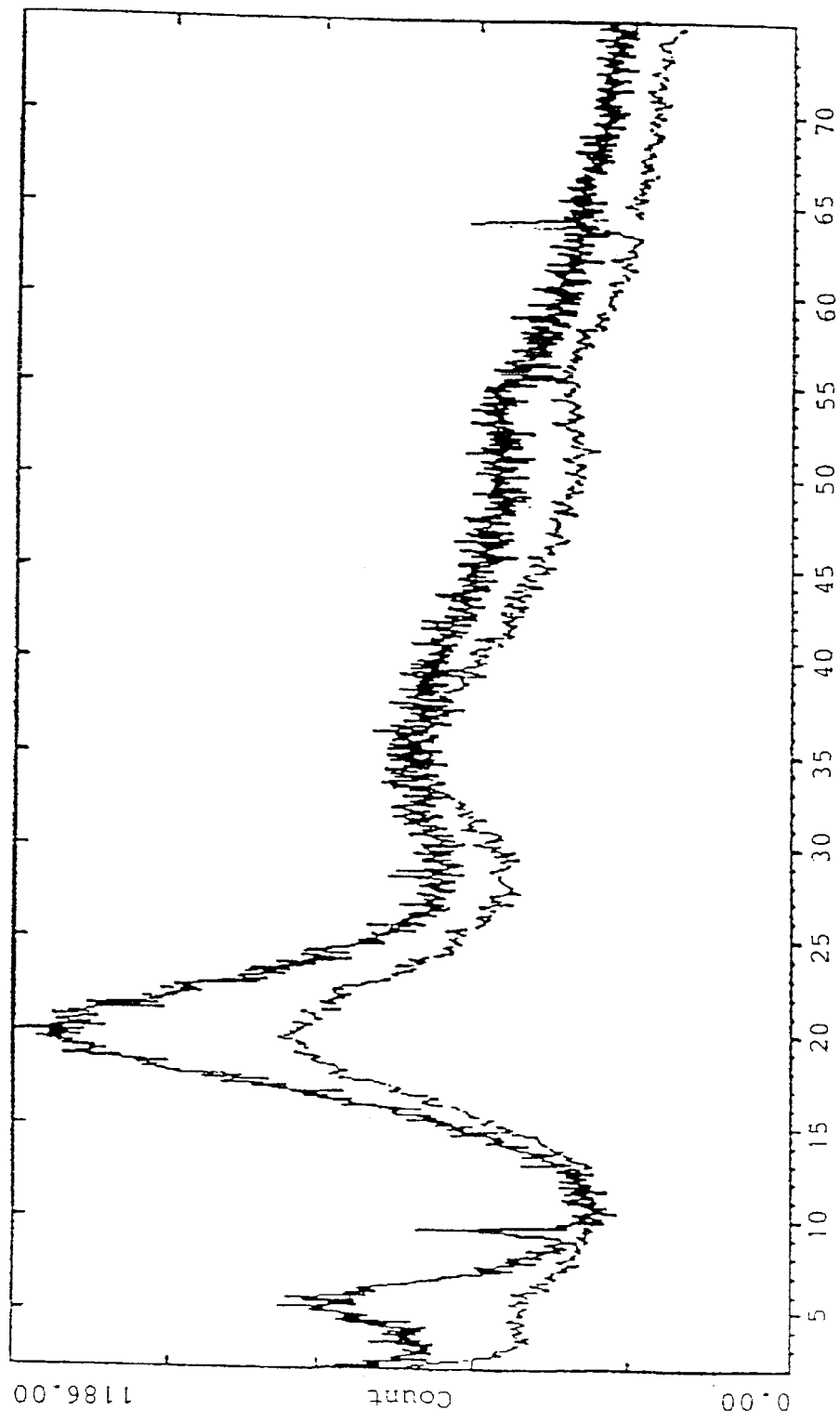
Figure 4. X-ray patterns of the Mg(OR)2 (Mg(OR)2)2/C7H16 + toluene complexes - in top curve the ROH is 2-ethyl-hexanol, in bottom curve ROH is n-butyl alcohol.

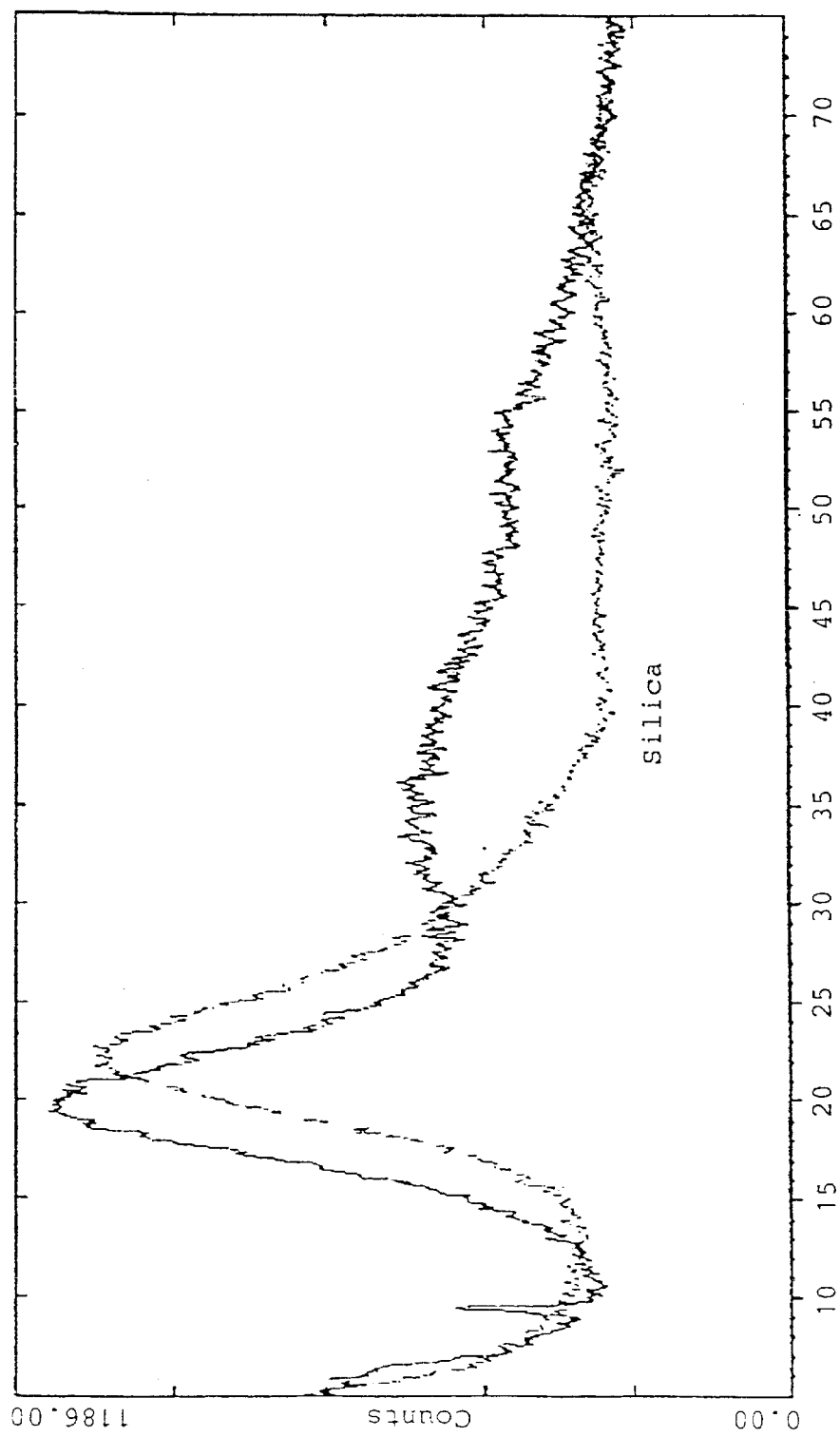
Figure 5. Comparison between a X-ray diffraction patterns of silica and a pattern of the $MgCl_2 \cdot (Mg(OR)_2)_2$.

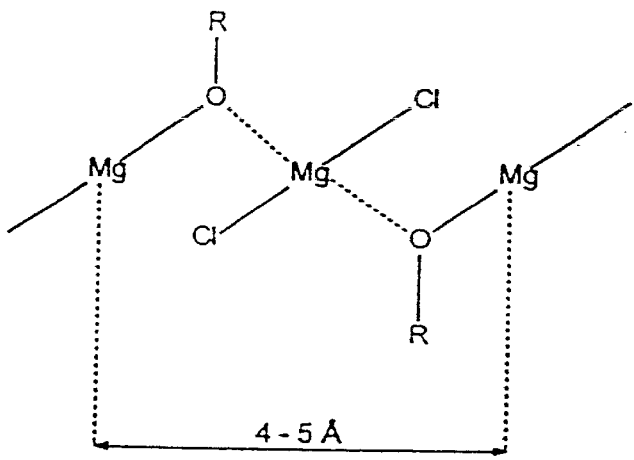
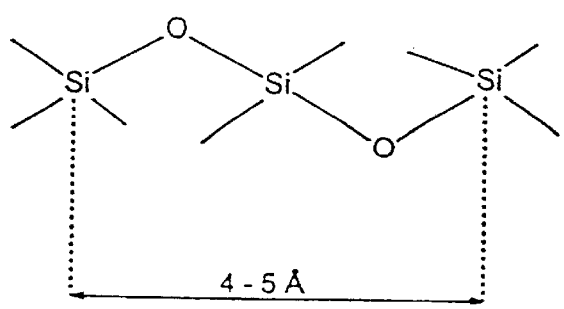
Figure 6. Resemblance of the reflecting distances in a complex $MgCl_2 \cdot (Mg(OR))_2$ compared to the construction of a Si-O-Si-O-Si silica material

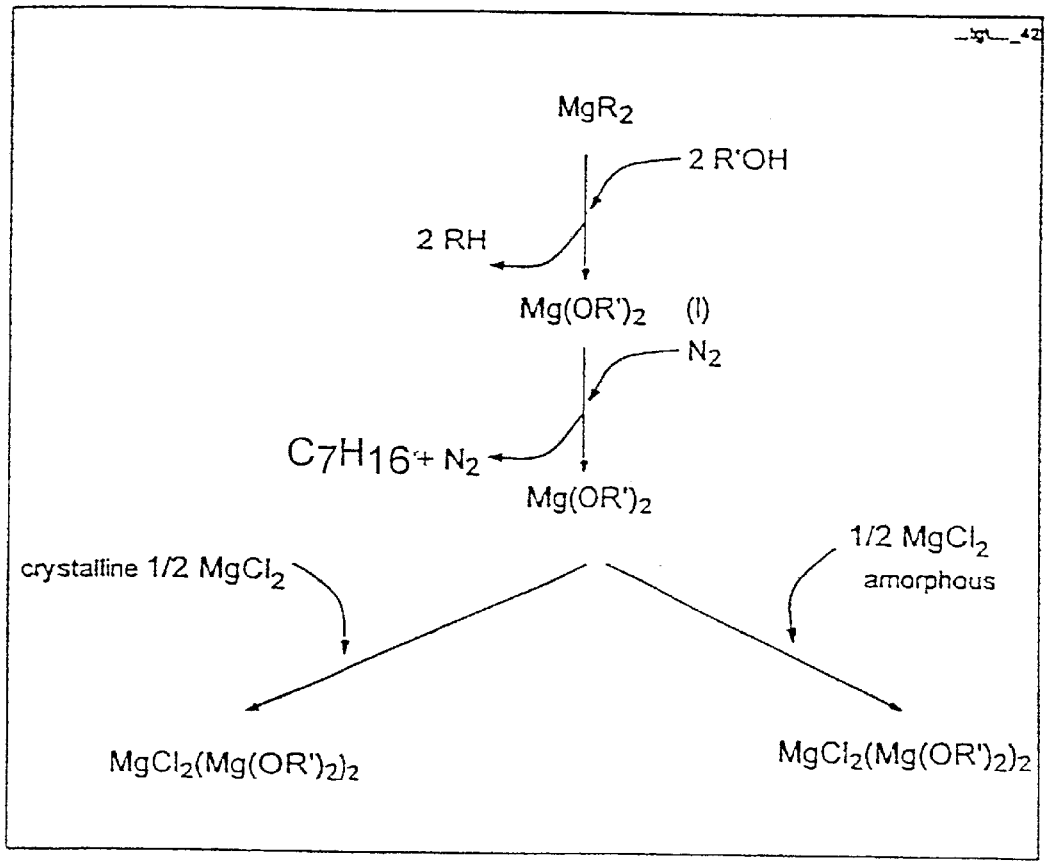
Figure 7. Principles for the preparation of the complexes achieved as mechanical blends between $MgCl_2$ and $Mg(OR)_2$

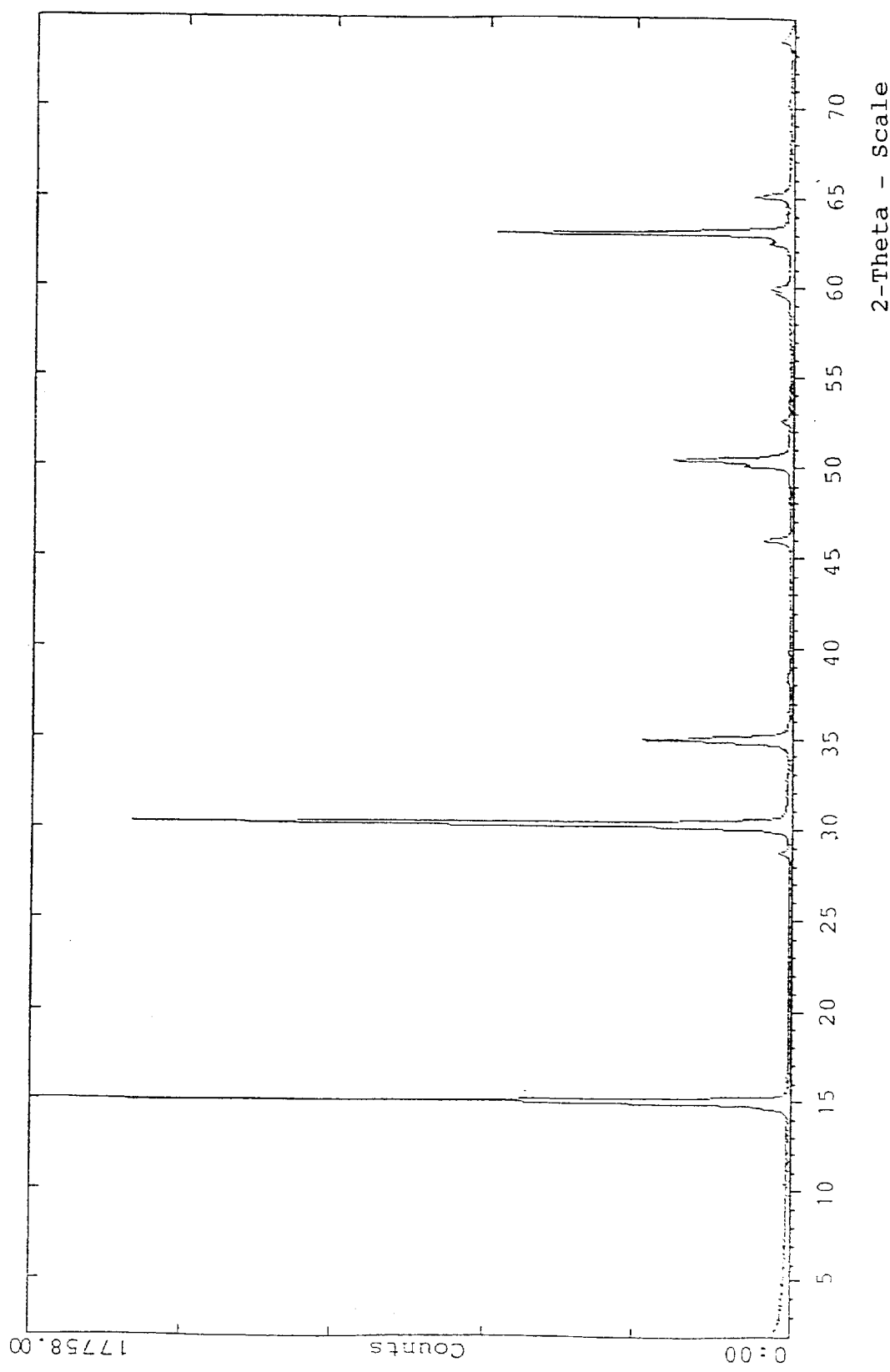
Figure 8. The X-ray diffraction pattern for chrystalline MgCl$_2$

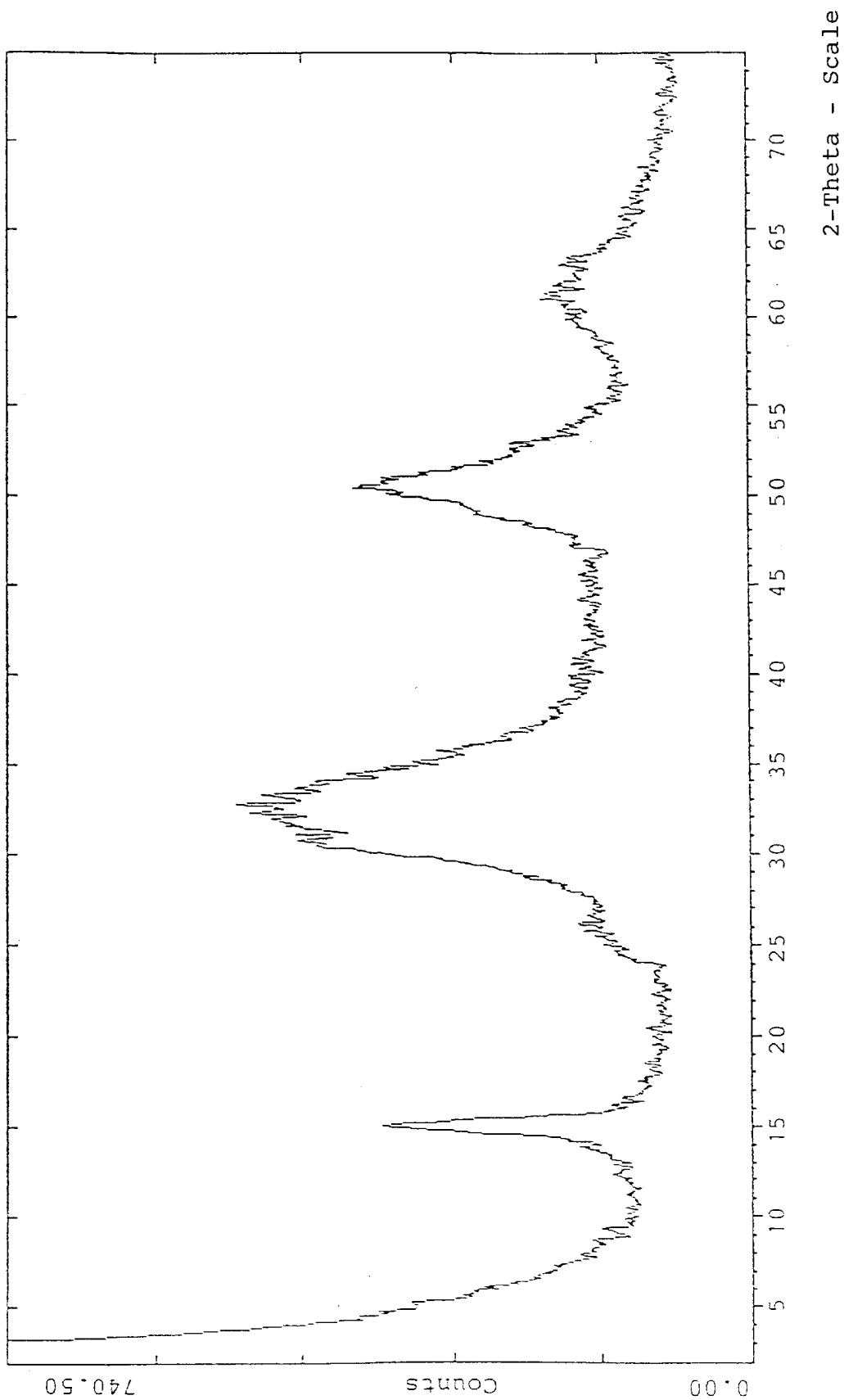
Figure 9. The X-ray diffraction pattern for amorphous MgCl2

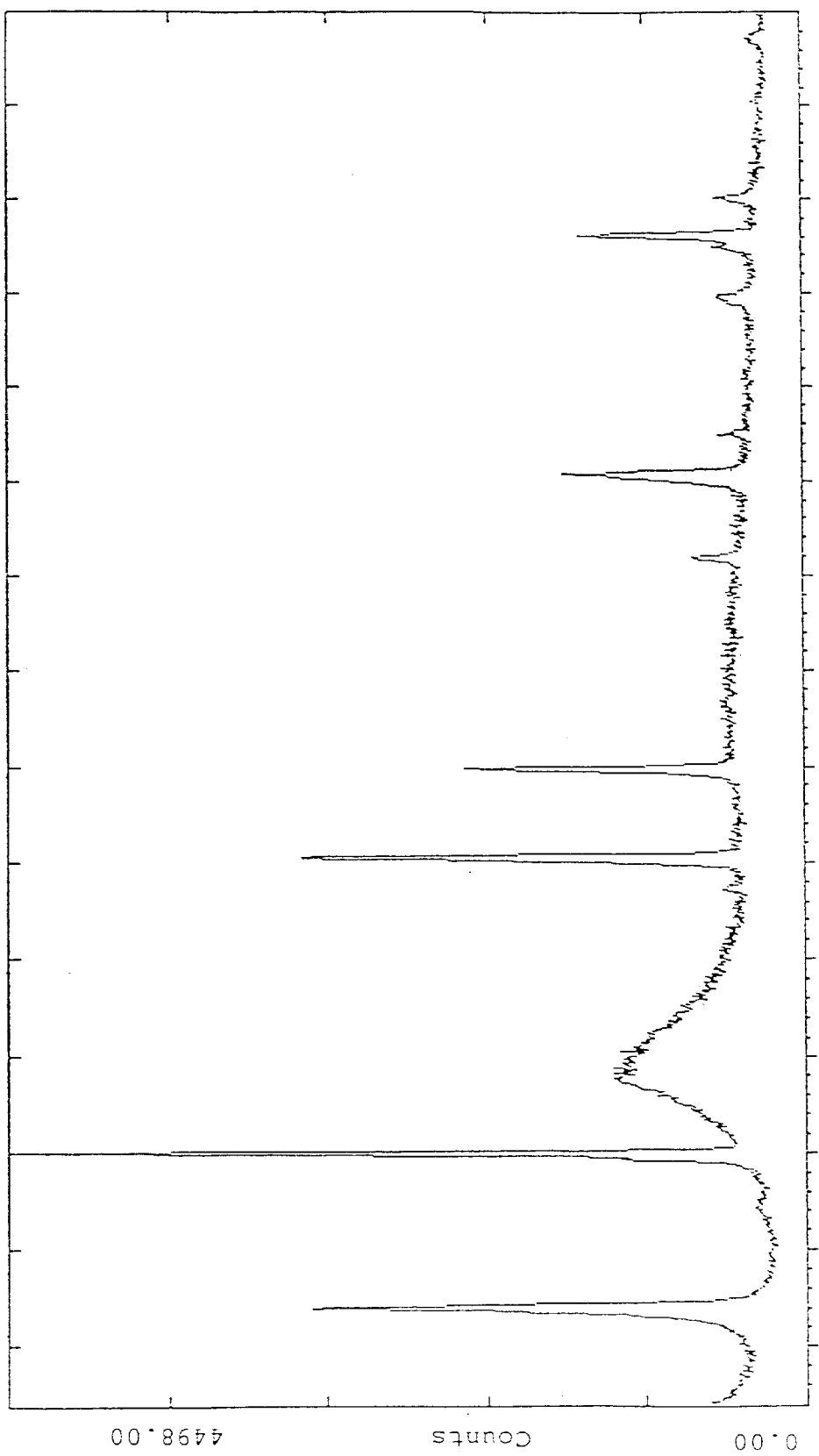
Figure 10. The X-ray diffraction pattern for the mechanical blend of chrystalline $MgCl_2$ and $Mg(OR)_2$

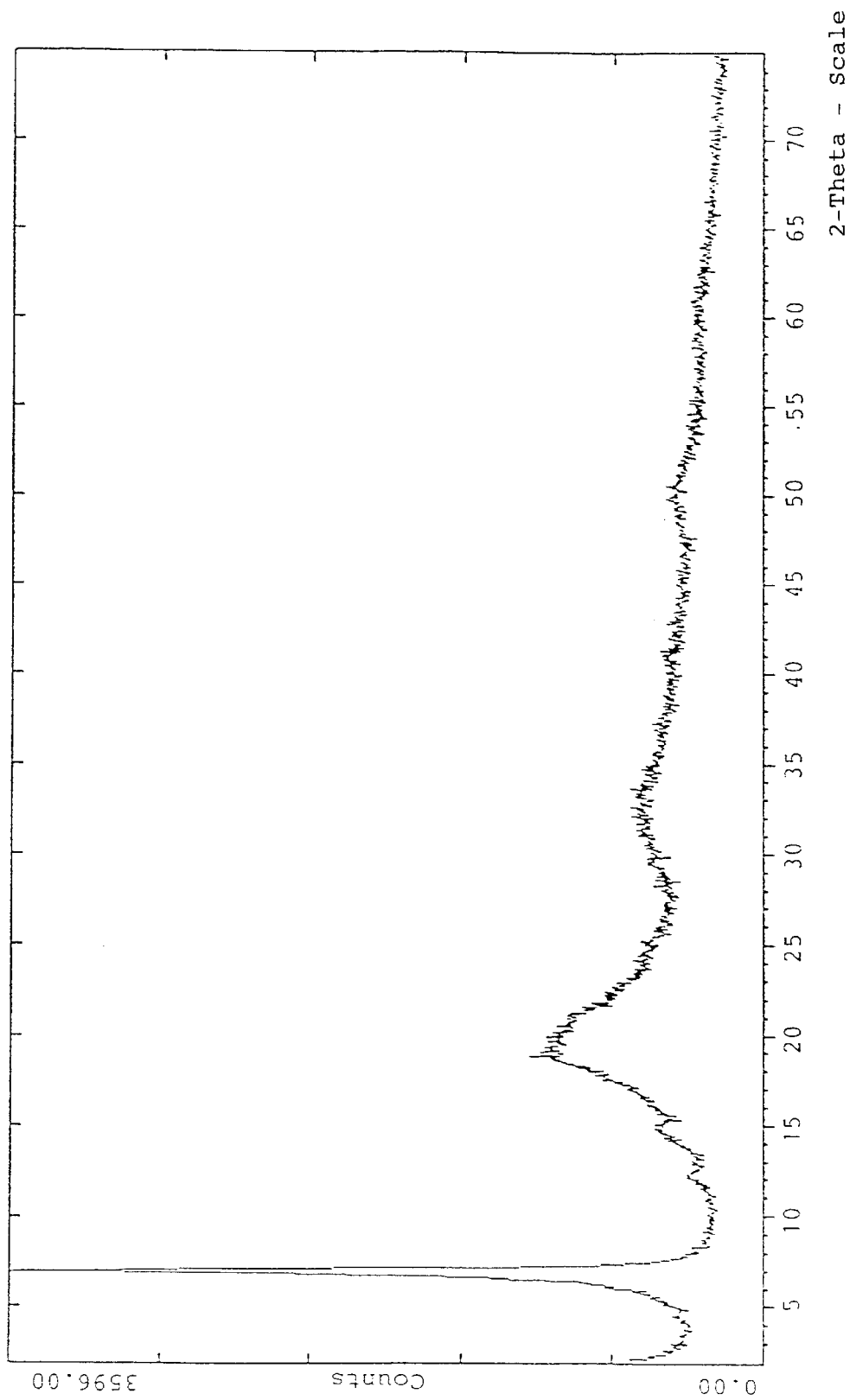
Figure 11. The X-ray diffraction pattern for the mechanical blend of amorphous MgCl$_2$ and Mg(OR)$_2$

PRODUCT CONTAINING MAGNESIUM, HALOGEN AND ALKOXY

This application is the national phase under 35 U.S.C. § 371 of PCT International Application No. PCT/FI98/01002 which has an International filing date of Dec. 21, 1998, which designated the United States of America.

The invention relates to a complex product containing magnesium, halogen and alkoxy. The invention also relates to a process for the preparation and use of such a complex product. By a complex product is meant either a distinct complex or a mixture of complexes.

To be able to activate magnesium with $TiCl_4$ to produce amorphous $MgCl_2$ for a Ziegler-Natta catalyst, the magnesium has to be brought in a reactive state with respect to $TiCl_4$. This is commonly done in two ways:

1. By forming a complex between $MgCl_2$ and an organic compound having an active hydrogen like an alcohol ROH. This $MgCl_2.mROH$ complex is allowed to react with $TiCl_4$. Thereby amorphous $MgCl_2^*$ is liberated. Equivalent amounts of titanous waste material: $TiCl_3OR$ and HCl are formed. This waste material has to be washed away with an excess of $TiCl_4$, which is a disadvantage.
2. By forming a Mg-alcoholate, i.e. $Mg(OR)_2$. This reacts with $TiCl_4$ to give amorphous $MgCl_2^*$. An equivalent of waste material, $TiCl_3OR$, is formed also here.

$MgR_2$ is soluble in inert hydrocarbon and reacts with $TiCl_4$ to give amorphous $MgCl_2^*$ but as $MgR_2$ is a strong reduction agent, an equivalent proportion of $TiCl_3$ is co-precipitated with the $MgCl_2^*$. The co-precipitation of $TiCl_3$ is a disadvantage when preparing a high yield polypropylene Ziegler-Natta catalyst.

With Grignard reagents like RMgCl and RMgBr, a strong solvent, i.e. an ether is needed to keep them in solution. If this kind of reagent is reacted with $TiCl_4$, amorphous $MgCl_2^*$ is formed but at the same time $TiCl_4$ complexates with all the R—O—R-oxygen atoms of the ether and a large amount of a catalytically inactive by-product complex $R_2O$—$TiCl_4$ is formed.

The reagents, reacting with $TiCl_4$ to give amorphous $MgCl_2^*$ are listed in Table 1. In Table 1, CH denotes hydrocarbon.

TABLE A

Reagents reacting with $TiCl_4$ giving amorphous $MgCl_2^*$

| Reagent | $MgCl_2.ROH$ | $Mg(OR)_2$ | $MgR_2$ | ClMgR |
|---|---|---|---|---|
| Solvent | CH | CH | CH | R—O—R |
| Reaction by product | $HClTiCl_3OR$ | $TiCl_3OR$ | $TiCl_3$ | $R_2O$—$TiCl_4$ |

According to Coates, G. E., et al., Principles of Organometallic Chemistry, Methuen & Co Ltd, London, 1971, pages 60 and 61, this type of complexes are prepared in diethyl ether, whereby e.g. a dimeric etherate is formed as follows:

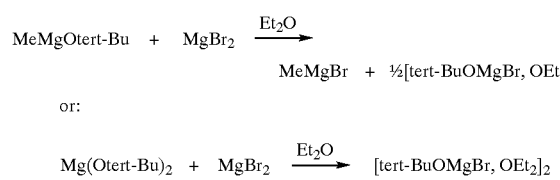

In the equation Me is methyl, Et is ethyl and tert-Bu is tertiary butyl. The etherate is dimeric in both benzene and ether media. The book also mentions that ether-free tert-BuOMgBr is insoluble in hydrocarbons and is likely to be polymeric. Tert-BuOMgCl can be assumed to behave in the same way, i.e. a strong polar solvent like an ether is needed to keep the reaction product in solution.

WO 92/16533 discloses a process for producing alkoxymagnesium halides in a single step by stoichoimetrically reacting magnesium alkyl activated magnesium with an equimolar mixture of an alkyl halogenide and an alcohol. However, in this process an additional equimolar amount of alcohol is added to the reaction media to bring the components into a liquid state in a inert hydrocarbon solution. The achieved solution is thus not RO.Mg.Cl but RO.Mg.Cl.ROH. This solution will in this way contain an equimolar amount of ROH that will react with $TiCl_4$ forming $TiCl_3OR$ and HCl in a typical catalyst synthesis where $TiCl_4$ is one of the reaction components.

The same situation can be seen in WO91/05608 where $MgCl_2$ is dissolved in 3ROH to produced $MgCl_2.3ROH$ that in turn is brought into contact with $Mg(OEt)_2$ to give an adduct of $MgCl_2.Mg(OEt)_2.3ROH$. 1.6ROH is then removed from this adduct by azeotropic evaporation with heptane to give a product of EtO.Mg.Cl.0.7ROH corresponding to the product described in WO92/16533.

WO 91/05608 added toluene and two different alcohols to magnesium chloride and refluxed for a short time. Then, dialkyl magnesium was added and the mixture was further refluxed. A complex of a magnesium haloalkoxide and two alcohols was obtained. Due to the alcohols in the complex, it was not suitable for the activation of $TiCl_4$, see above.

U.S. Pat. No. 4,727,051 reacted $MgCl_2$-ROH complexes and obtained stoichiometric compositions without giving their chemical structure.

When using dissolved magnesium compounds for the activation of the transition metal compound of a Ziegler-Natta procatalyst, such as magnesium chloride, $MgCl_2$, dissolved in a polar solvent, or magnesium alkyl, $MgR_2$ or RMgCl, dissolved in diethyl ether or a hydrocarbon, other problems arise. In the case of $MgCl_2$, problems are caused by the large amount of polar solvent needed for dissolving $MgCl_2$. Evaporation operations of the polar solvent during the process of procatalyst preparation are laborous and, besides, traces of polar solvent on the formed procatalyst has to be removed by separate chemical treatment. In the case of $MgR_2$, if not reacted with $TiCl_4$, a separate chlorination agent and a separate chlorination step is need for activation. In addition to this $MgR_2$ and RMgCl have the drawback that they easily overreduce the transition metal and have to be modified to a less reductive form, e.g. to a magnesium alkoholate $Mg(OR)_2$, before use.

When preparing the procatalyst from starting materials which will react into a final catalytically active complex, i.e. by means of a stoichiometric process, the product generally tends to have unsufficiently Mg and Cl (or other halogen) for satisfactory activity. Thus there is a need for starting materials having an enhanced amount of Mg and Cl (or other halogen) in their molecules.

One purpose of the invention is to provide a soluble magnesium compound, which gives good activity and is soluble in non-polar solvents. The magnesium compound must not overreduce the transition metal, because overreduction leads to low procatalyst activity. Another independent purpose of the invention is to provide a molecule, which contains sufficiently Mg and Cl (or other halogen) to produce high catalytic activity when reacted stoichiometrically with other compounds into a procatalyst or a complete Ziegler-Natta catalyst system.

The above problems have now been eliminated and the purposes fulfilled with a complex product containing magnesium, halogen and alkoxy, essentially characterised by having the following formula (1):

$$Mg_pX_q(OR)_{2p-q} \quad (1)$$

wherein X is a halogen, preferably a chlorine, R is an alkyl group having from 1 to 20 carbon atoms, p is from 2 to 20 and q is <p, preferably <0.66 p. If there are several halogens X and alkoxy groups OR in the complex product, they can be different or equal.

The complex product according to the invention can, depending on the quality and quantity of elements and groups, be soluble in non-polar organic solvents. Thus, complexes which are both soluble and insoluble in non-polar solvents can be selected among the claimed complexes. The soluble complexes can e.g. be used as starting material for catalytically active stoichiometrical procatalyst complexes and the insoluble complexes can e.g. be used as supporting activators of the transition metal compounds. Further, the complex product of the invention is always less reductive than the above mentioned magnesium alkyls $MgR_2$ and RMgX and is therefore more suitable for activation of the transition metal compound. The complex product has, even at its smallest Mg (p=2) and X (q=1) contents, more magnesium and halogen in its molecule unit than the above mentioned non-reductive $Mg(OR)_2$. Whereas $Mg(OR)_2$ has Mg:X:OR=1:0:2, the claimed complex has at least the ratio M:X:OR=2:1:3.

The chemical structure of the claimed complex product is based on the bivalence and bridge-forming ability of magnesium. It is believed, without limiting the scope of the invention, that the chemical structure is (a):

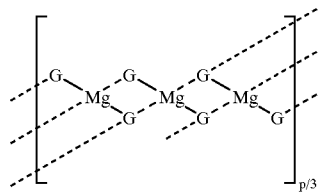

(a)

wherein each G is the same or different and is selected from said X and said OR to form q units of X and 2p–q units of OR, and p is from 3 to 20. If p/3 is greater than 1 there is in formula (a) a . . . —bridge from the furthest Mg—G to the nearest M—G of the next unit.

The chemical structure can also be (b):

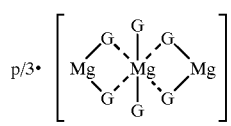

(b)

wherein each G is the same or different and is selected from said X and said OR to form q units of X and 2p–q units of OR, and p is from 3 to 20, or (c):

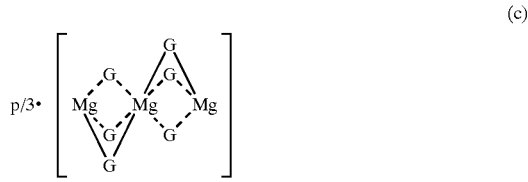

(c)

wherein each G is the same or different and is selected from said X and said OR to form q units of X and 2p–q units of OR, and p is from 3 to 20.

Most probably the claimed complex product has the structure of an equilibrium between structures (a), (b) and (c), as illustrated by the following trimer equilibrium of a $MgCl_2 \cdot [Mg(OR)_2]_2$ complex:

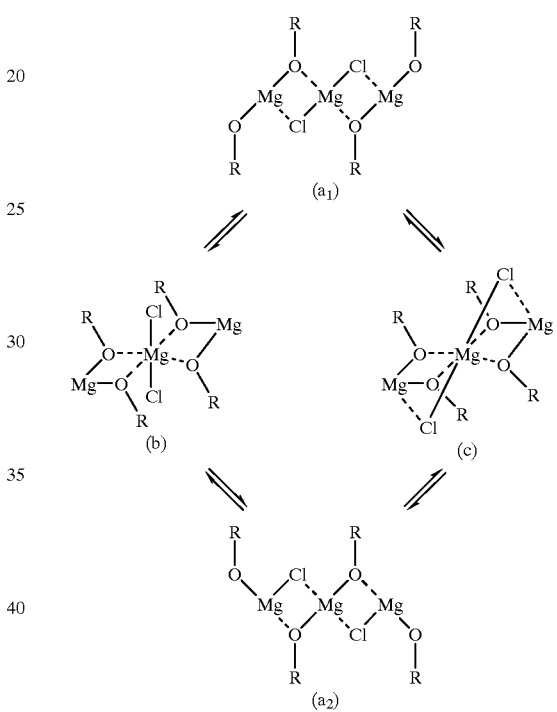

In the above formulas (a₁), (a₂), (b) and (c), Cl can be replaced by any halogen such as fluorine, chlorine, bromine and iodine, but the purposes of the invention are best fulfilled with chlorine.

The alkyl R of the alkoxy group can be any alkyl suitable for the purpose of the invention. Similar structure and solubility parameter to optional solvents give soluble complexes for stoichiometric preparation of active procatalyst complexes. Different structure and solubility parameters give insoluble complexes for use as activating support. When a solvent having 5–10 carbon atoms, such as toluene, is used, R is preferably an alkyl group having from 1 to 16 carbon atoms, more preferably from 4 to 12 carbon atoms, most preferably from 6 to 10 carbon atoms.

In the above formulas (a₁), (a₂), (b) and (c), p is chosen depending on the complex product's purpose of use. A higher oligomer (p≥5) is less soluble and is suitable as supporting reagent, whereas e.g. a di-, tri- or tetramer is more soluble and suitable for e.g. homogenous and stoichiometric procatalyst preparation. Generally, p is preferably from 2 or 3 to 20, more preferably from 2 or 3 to 10. For homogenous and stoichoimetric preparation, p is preferably from 2 or 3 to 6, more preferably from 2 or 3 to 4, and most preferably 3.

The number of halogens in the molecule agglomerate of the complex product can vary very much. As was initially established, a large amount of chlorine leads to insolubility in non-polar solvents, whereas good activity requires a large amount of halogen. This means that the amount of halogen has to be balanced. According to one embodiment, q is from 2 to p, preferably 2 (when p is 3).

According to a preferable embodiment of the invention, the formula and structure of the claimed complex product is such that it is soluble in a non-polar solvent, preferably in a hydrocarbon, more preferably in an aromatic hydrocarbon, most preferably in toluene.

Above, the claimed complex product has been described by means of its formula, probable structure and solubility. It is also proper to describe it according to its empirical, i.e. analytical composition. The claimed complex product preferably has the following empirical (Mg=1) composition (2):

$$MgX_a(OR)_b \qquad (2)$$

wherein X and R are the same as above, a is 0.4–1.2 and b is 0.8 to 1.6.

According to Römpps Chemie-Lexikon, 7. Ed., Franckh'she Verlagshandlung, W. Keller & Co., Stuttgart, 1973, Band 3, page 1831, a complex is a "derived name for compounds of higher order, which compounds are formed from molecules—in contrast to the compounds of first order, in the formation of which atoms participate". According to one embodiment of the invention, the claimed complex product is e.g. formed from the molecules $MgCl_2$ and $Mg(OR)_2$ or $ROMgCl$ and $Mg(OR)_2$. For example, it is a complex having a composition corresponding to the following formula (3):

$$[MgCl_2]_{q/2} \cdot [Mg(OR)_2]_{p-q/2} \qquad (3)$$

wherein R, p and q are the same as above. Most preferably q is 2, i.e. it has a composition corresponding to the formula (4):

$$MgCl_2 \cdot [Mg(OR)_2]_2 \qquad (4)$$

wherein R is the same as above.

An important characteristic and feature of the claimed complex product is that it shows a X-ray diffraction pattern having a halo between 14° and 26° 2Θ, more specifically between 18° and 22° 2Θ. The halo formation observed in the pattern of $MgCl_2 \cdot [Mg(OR)_2]_2$ separates this complex from $Mg(OR)_2$, $MgCl_2 \cdot 2ROH$, $MgCl_2$. $C_6H_4(COOR)_2$ and $(MgCl_2)_2 \cdot TiCl_4 \cdot C_6H_4(COOR)_2$ ($C_6H_4(COOR)_2$ is a typical internal phthalate electron donor), which all have a sharp distinct peak between 5° and 10° 2Θ, but no halo formation between 18° and 22° 2Θ.

The invention also relates to a process for the preparation of a complex product containing magnesium, halogen and alkoxy. In the process a magnesium dihalide, an alcohol having from 1 to 20 carbon atoms and a dialkyl magnesium having from 2 to 40 carbon atoms are reacted to form said complex product.

It is preferable in the claimed process, that said magnesium dihalide is magnesium dichloride. Preferably, said alcohol is a compound of the formula ROH wherein R is an alkyl having 1 to 16 carbon atoms, preferably 4 to 12 carbon atoms, most preferably 6 to 10 carbon atoms. Said dialkyl magnesium is a compound of the formula $MgR'_2$, wherein each R' is the same or different and is an alkyl with 1 to 20 carbon atoms, preferably 2 to 12 carbon atoms, most preferably 4 to 10 carbon atoms.

Said complex product is preferably a complex product according to the above description.

The claimed preparation process preferably has two steps. The process comprises:
a) reacting said magnesium dihalide and said alcohol into an intermediate in liquid form,
b) reacting said intermediate in liquid form with said dialkyl magnesium into said complex.

Without limiting the scope of protection, the process can be described by the following equation:

$$MgCl_2 + 4ROH \rightarrow MgCl_2 \cdot 4ROH$$

$$MgCl_2 \cdot 4ROH + 2MgR'_2 \rightarrow MgCl_2[Mg(OR)_2]_2 + 4R'H$$

In step a) of the two-step process of the invention, said magnesium halide and said alcohol are preferably reacted in a molar ratio of 1:2 to 1:8, more preferably 1:3 to 1:5, most preferably about 1:4. The magnesium halide and the alcohol are preferably reacted at 100 to 200° C., most preferably at 110 to 150° C. The reaction time between the alcohol and the magnesium halide is preferably 1 to 8 h, most preferably for 2 to 6 h.

According to one embodiment a solvent, preferably a hydrocarbon, more preferably an aromatic hydrocarbon, most preferably toluene, is added to keep said intermediate in liquid form. The amount of solvent is preferably such that said magnesium halide and said solvent are used in a molar ratio of 1:4–1:100, more preferably 1:10–1:40, most preferably 1:12–1:24.

In step b) of the claimed process said magnesium halide and said dialkyl magnesium are preferably used in a molar ratio of 1:1 to 1:4, preferably about 1:2. It is advantageous, if said dialkyl magnesium is provided in the form of a solution, preferably a hydrocarbon solution, most preferably a hydrocarbon solution having a molar ratio between said dialkyl magnesium and the hydrocarbon of said solution of 1:2 to 1:10, preferably 1:4 to 1:8. The hydrogen of said hydrocarbon solution is preferably a hydrocarbon having 5 to 12 carbon atoms, most preferably an aliphatic or aromatic hydrocarbon having 6 to 10 carbon atoms.

According to the product description above, the complex product is preferably soluble so that an active procatalyst complex can be prepared directly by reacting the starting materials with each other. This means, that in the claimed preparation process, said reaction product is recovered in the form of a solution in said solvent or solvents.

According to the initially defined purpose of the invention, the claimed complex product is used for the preparation of an olefin polymerisation catalyst, preferably the transition metal component of an olefin polymerisation catalyst, most preferably the titanium component of an olefin polymerisation catalyst. Naturally, the invention also relates to such a use. More specifically, said complex product is reacted with a titanium compound and preferably with an electron donor compound into said titanium component of an olefin polymerisation catalyst.

As was also initially stated, said complex or a reaction product thereof is according to one embodiment of the invention in liquid form and preferably impregnated on an organic or inorganic catalyst support, more preferably an inert support, even more preferably an inorganic inert support such as silica, alumina, a mixed oxide or mixture thereof, and most preferably silica.

According to another embodiment of the invention, said complex is in the form of an insoluble polymeric complex, acting as Mg provider and catalyst support.

Experimental

In the following the invention is exemplified, wherein the following figures are referred to:

FIG. 1 shows the principles for preparing a solution containing the claimed complex.

FIG. 2 shows the X-ray diffraction patterns of $Mg(OR)_2$ (12.5 Å) and for the $MgCl_2 \cdot 2ROH$ (13.5 Å).

FIG. 3 shows most probable complexation of $Mg(OR)_2$ giving a 12.5 Å distance between Mg.

FIG. 4 shows the X-ray patterns of $MgCl_2 \cdot [Mg(OR)_2]_2 / C_7H_{16}$+toluene complexes—in top curve the ROH is 2-ethyl-hexanol, in bottom curve ROH is n-butyl alcohol.

FIG. 5 shows comparison between X-ray diffraction patterns of silica and a pattern of the $MgCl_2 \cdot (Mg(OR)_2)_2$.

FIG. 6 shows resemblance of the reflecting distances in a complex $MgCl_2 \cdot Mg(OR)_2$ compared to the construction of the Si—O—Si—O—Si silica material.

FIG. 7 shows the principles of preparing complexes of the reference by blending mechanically $MgCl_2$ and $Mg(OR)_2$.

FIG. 8 shows the X-ray diffraction pattern for crystalline $MgCl_2$.

FIG. 9 shows the X-ray diffraction pattern for amorphous $MgCl_2$.

FIG. 10 shows the X-ray diffraction pattern for a mechanical blend of crystalline $MgCl_2$ and $Mg(OR)_2$.

FIG. 11 shows the X-ray diffraction pattern for a mechanical blend of amorphous $MgCl_2$ and $Mg(OR)_2$.

EXAMPLES

In Table 1 the set up of the experimental test series is shown. Three different alcohols ROH were used, namely butanol (BuOH), 2-ethyl-hexanol (EHA) and undecanol (UDOH). Toluene was used to improve the solubility of the complex. The synthesis was started by introducing 0.03151 mol (3.0 g) of $MgCl_2$ into the reactor. 0.12606 mol of the appropriate alcohol was added on the $MgCl_2$. The reactants were mixed at 130° C. for 4 h to create a clear melt. When the $MgCl_2$—ROH melt was achieved toluene was added. The added amount of toluene was between 20 ml and 100 ml, 0.06372 mol of dialkyl magnesium $MgR'_2$ was now added. A 20% heptane solution butyl-octyl-magnesium (BOMAG A) was used, thus giving a feed volume of 72 ml (52.5 g). Depending on the test conditions, some toluene was added also after the addition of the Mg-alkyl. All the chemicals added in the experiments are listed as equivalent amounts in Table 1.

The resulting complexes were characterised by IR and X-ray spectroscopy and by determining their chemical composition. In addition to the full synthesis of the $MgCl_2 \cdot [Mg(OR)_2]_2$ three tests were carried out involving only the dissolutions of $MgCl_2$ into various amounts of the alcohol to see to what extent $MgCl_2$ is dissolving in the alcohol. Three dissolution tests were carried out and in each case 3.0 g $MgCl_2$ was introduced into the reactor. Successively smaller portions of EHA alcohol was added on to the $MgCl_2$. The $EHA/MgCl_2$ molar ratios used were 4, 3.3 and 2.9. In each case the $MgCl_2$ was allowed to come to an equilibrium with the alcohol during 6 h. Samples were taken from the clear solutions and the Mg and Cl contents were measured from these solutions. The resulting samples were also characterised by IR and X-ray spectroscopy.

Finally, the complexes were used for the preparation of transition metal catalyst components of olefin polymerisation catalysts.

TABLE 1

The added chemicals expressed in chemical equivalents in the experimental series.

| Added component | Example 1 | Example 2 | Example 3 | Example 4 | Example 5 | Example 6 | Example 7 |
|---|---|---|---|---|---|---|---|
| $MgCl_2$ | 1 | 1 | 1 | 1 | 1 | 1 | 1 |
| BuOH | — | — | — | 4 | — | — | — |
| EHA | 4 | 4 | — | — | 3.3 | 2.9 | 4 |
| UDOH | — | — | 4 | — | — | — | — |
| Toluene | 18 | 8 | 18 | 6 | — | — | — |
| $MgR_2$ | 2 | 2 | 2 | 2 | — | — | — |
| Heptane | 13 | 13 | 13 | 13 | — | — | — |
| Toluene | — | 10 | 12 | — | — | — | — |

Results and Discussion

A liquid complex was not prepared in all the examples of this series. In the first example (1), the $MgCl_2$ dissolved well in the alcohol ROH. The toluene decreased the viscosity of the resulting solution. The viscosity remained low during the first part of the $MgR'_2$ addition. After ⅔ of the $MgR'_2$ had been added there was a clear increase in viscosity. The reaction solution demanded harder mixing to stay in motion.

In the next example (2) the recipe from the first test was repeated with the exception that less toluene was used in the preparation. As in the first synthesis the $MgCl_2$ dissolved well in the alcohol (+130° C., 3.5 h). The toluene addition decreased the viscosity of the solution. The reaction solution stays as a liquid at the beginning of the $MgR'_2$ addition. When ⅔ of the $MgR'_2$ had been added the solution turned into a solid. It was not possible to dissolve the solid with further toluene addition. This complex was not further investigated. This experiment showed that it was not possible to redissolve the complex by toluene addition, once the complex had been solidified.

In the third example (3) undecanol was used as alcohol. The $MgCl_2$ dissolved in this alcohol at 130° C. but it solidified again when the temperature of the melt decreased. A totally clear liquid was achieved when toluene was added. Viscosity increased when the $MgR'_2$ was added but as long as less than ⅔ of the $MgR'_2$ had been added the solution was freely flowing. When more than ⅔ of the $MgR'_2$ had been added the reaction mixture became solid. It was not possible to redissolve the mixture by adding more toluene to the reaction slurry. This complex was not further investigated.

In the fourth example (4) butanol was used as alcohol to see if the $MgCl_2$ enriched complex $MgCl_2 \cdot [Mg(OR)_2]_2$ could be prepared using this alcohol. Also in this case the $MgCl_2$ was able to dissolve at 130° C., at 20° C. it turned back into a solid. Toluene addition brought the compound back to solution at 100° C., but at 20° C. it was still partly solid. When adding the $MgR'_2$, the reaction components stayed as a clear solution until ⅔ of the $MgR'_2$ had been added after which some flakes or agglomerates could be seen in the solution. This complex was however considered to be good enough in impregnating a support material to qualify it for further characterisation.

In the dissolving tests (examples 5, 6 and 7) it turned out that a full dissolution of the $MgCl_2$ in the EHA alcohol could be achieved only in the case when the $ROH/MgCl_2$ molar ratio was 4 (ex. 7). In the case less alcohol had been used, i.e. the $ROH/MgCl_2$ molar ratio was 3.3 (ex. 5) or 2.9 (ex. 6) some $MgCl_2$ remained undissolved in the bottom of the reactor. In table 2, a summary of the reaction conditions are listed for all the syntheses.

TABLE 2

Summary of the reaction conditions in the syntheses.

| Added component | Example 1 | Example 2 | Example 3 | Example 4 | Example 5 | Example 6 | Example 7 |
|---|---|---|---|---|---|---|---|
| $MgCl_2$ 4BuOH | Solid | Solid | Solid | Solid Liquid at 130° C. solid at 20° C. | Solid | Solid | Solid |
| 4EHA or less | Liquid at 130° C. | Liquid at 130° C. solid at 20° C. | | | Partly undissolved $MgCl_2$ | Partly undissolved $MgCl_2$ | Liquid at 130° C. |
| 4UDOH | | | Liquid at 130° C. solid at 20° C. | | | | |
| Toluene | Liquid | Liquid | Liquid | Liquid at 100° C. solids at 20° C. | | | |
| Up to 2/3 $MgR_2$ added | Liquid, exotherm reaction | Liquid | Viscose liquid | Liquid | | | |
| All $MgR_2$ added | High viscosity | Solid | Solid | Liquid with solids | | | |
| Additional toluene | | Gels, partly solid | Solid | | | | |

Chemical Composition of the Complexes

In table 3 the chemical composition of the $MgCl_2$ enriched Mg-alcoholates are listed together with the Mg and Cl concentrations of the $MgCl_2$ dissolving tests. In a normal Mg-alcoholate compound there is a Mg/RO-molar ratio of 1:2, and a Mg/Cl molar ratio of 1/0. In this study we have created a $MgCl_2$ enriched version of a Mg-alcoholate with a chemical composition of $MgCl_2[Mg(OR)_2]_2$ having the Mg/Cl/RO-molar ratios of 3:2:4 or 1/0.67/1.33. The molar composition of the complexes were calculated from the analytical figures of table 3 and compared to the calculated figures. The results are given in table 4. The results show quite good agreement with the calculated values. The Cl amounts found in the complexes were a little too high but the alcohol amounts corresponded almost totally to what could be expected on the basis of the calculations. These results showed that it is possible. to create a much $MgCl_2$-richer complex by using pre addition of $MgCl_2$ to the alcohol when preparing the Mg-alcoholate. The Mg/Cl/RO-ratio can be brought up from 1:0:2 to 1:0.7:1.3. The dissolution tests showed that it was possible to dissolve only a little more $MgCl_2$ in the EHA alcohol when increasing the $MgCl_2$ concentration. In the standard test (ex. 7) the achieved Mg % was 3.9, while it was between 4.1% and 4.2% in the alcohol melt solutions where a proportionally higher degree of $MgCl_2$ had been present.

TABLE 3

The chemical composition of the complexes

| Complex | Mg (w-%) | Cl (w-%) | BuOH (w-%) | EHA (w-%) |
|---|---|---|---|---|
| Example 1 | 2.0 | 2.1 | | 13.6 14.5 |
| Example 4 | 1.7 | 2.4 | 6.8 | |
| Example 5 | 4.2 | 13.2 | | 88.5 |

TABLE 3-continued

The chemical composition of the complexes

| Complex | Mg (w-%) | Cl (w-%) | BuOH (w-%) | EHA (w-%) |
|---|---|---|---|---|
| Example 6 | 4.1 | 13.2 | | 88.8 |
| Example 7 | 3.9 | 11.9 | | |

TABLE 4

The molar ratios between Mg, Cl and ROH

| Complex | Mg | Cl | ROH |
|---|---|---|---|
| Calculated | 1 | 0.67 | 1.33 |
| Example 1 | 1 | 0.72 | 1.27 1.35 |
| Example 4 | 1 | 0.97 | 1.31 |

X-ray pattern of $Mg(OR)_2$ and of $MgCl_2.2ROH$ (R=2-ethylhexyl, comparative analysis)

In FIG. 2, the X-ray diffraction pattern of $MgCl_2.2ROH$ is shown together with the corresponding pattern for $Mg(OR)_2$. The patterns are strongly related in that they show a strong reflection peak in the 6° to 7° 2Θ region, indicating that the reflecting Mg layers are separated by large organic groups. In both cases the crystal structure is "one dimensional" as almost no indications of reflecting planes in the side direction can be seen; the construction is "needle" like.

The position of the $Mg(OR)_2$ peak indicates that the Mg is regularly separated by a distance of 12.5 Å. This suggests a construction for the $Mg(OR)_2$ crystals where the Mg atoms are separated by the 2-ethyl-hexanolate groups that are lying side by side in a partial crystallisation. This regular construction is causing the appearance of the regular reflection at 7° 2Θ (FIG. 3). The ethyl groups in the 2 position is preventing the compound to orientate in the side direction.

The $MgCl_2.2ROH$ peak indicates that the Mg in these crystals are regularly separated by a distance of 13.5 Å. This in turn indicates a construction for the $MgCl_2.2ROH$ crystals where the Mg atoms are separated by the complexated 2-ethyl-hexanol molecules that are lying side by side in a partial crystallisation. This regular construction is causing the appearance of the regular reflection at 6° 2Θ. The sightly longer distance between the Mg atoms in these crystals compared to the distance in the $Mg(OR)_2$ would be due to the fact that the hexanol is only complexated to the $MgCl_2$ while the oxygen is bound by a covalent bond to the Mg in the $Mg(OR)_2$ molecule giving a somewhat shorter distance. The ethyl groups in the 2 position is preventing also in this case the compound to orientate in the side direction.

X-ray diffraction patterns of the $MgCl_2$ enriched Mg-alcoholates (according to the invention)

In FIG. 4 is shown the X-ray diffraction pattern for the $MgCl_2.[Mg(—O-2-ethyl-hexyl)_2]_2$ (ex. 1) complex and of the $MgCl_2.[Mg(—O—But)_2]_2$ complex (ex. 4). In both cases there is a distinct halo formation between 18° and 22° 2Θ. There is no sign of the typical $MgCl_2$ peaks at 15°, 30°, 35° and 50° 2Θ. The distinct peaks seen at 5°–9° 2Θ in the patterns for the $Mg(OR)_2$ and for the $MgCl_2.2ROH$ are also almost missing in the patterns for these two $MgCl_2$ enriched complexes. In the product of example 1 there is only a minor peak at 10° 2Θ and a small halo formation at 6°–7° 2Θ, in the other complex (ex. 4) pattern no peaks are detectable at all in the narrow angle region.

Strong resemblance to silica diffraction patterns

In FIG. 5 the $MgCl_2.[Mg(OR)_2]_2$, wherein R is 2-ethylhexyl, diffraction pattern is compared to a typical silica (Grace silica 432, calcinated at 600° C. for 14 h) diffraction pattern. There is a clear resemblance in that both patterns show a halo between 18° and 22° 2Θ. A reflection at 18° 2Θ refers to a reflection distance of 4.9 Å and at 22° to a reflection distance of 4.0 Å. This indicates that there are reflecting atoms on a distance that corresponds to 4–5 molecular bonds. In the case of the $MgCl_2.[Mg(OR)_2]_2$ diffraction pattern the reflection can be caused by Mg atoms in the alcoholate groups surrounding the $MgCl_2$ in the middle (see FIG. 7). In the case of the silica the same reflection distance can form between two Si atoms separated by a —O—Si—O— unit, i.e. this unit should give a little bit shorter distance as the atoms are united by chemical bonds and not as in the Mg-complex partly by complexation. This difference in bond nature can explain why the silica halo is somewhat more to the right on the reflection angle scale compared to the halo of the $MgCl_2[Mg(OR)_2]_2$ diffraction pattern (FIG. 6).

Comparative Examples A and B

Above we disclosed the preparation of the complex $MgCl_2(Mg(OR)_2)_2$, in which R is 2-ethylhexyl. Here the $MgCl_2$ enriched Mg(OR)2 was achieved by first dissolving $MgCl_2$ in the alcohol ROH and then reacting this solution with $MgR_2$. The $MgCl_2(MgCl(OR)_2)_2$ complex formed in this synthesis showed a characteristic X-ray diffraction pattern whith a large halo between 18° and 220° 2Θ. In this investigation we are trying to prepare a $MgCl_2$ enriched $Mg(OR)_2$ trough mechanical blends of these two components. The two components are mixed in the same proportions as they appear in the $MgCl_2(MgCl(OR)_2)_2$ complex.

Experimental

Mechanical blend of crystalline $MgCl_2$ and $Mg(OR)_2$, wherein R is 2-ethylhexyl 1.0 g (3.537 mmol) of the produced $Mg(OR)_2$ was introduced into a 50 ml glass reactor. 168.6 mg (1.771 mmol) of crystalline $MgCl_2$ was added on to this and the mixture was allowed to merge together during constant mixing. The idea was to create the same molar composition in this mechanical blend as was in the $MgCl_2$ enriched $Mg(OR)_2$ described in our earlier report of RD6797, i.e. $MgCl_2(Mg(OR)_2)_2$. enriched $Mg(OR)_2$ described in our earlier report of RD6797, i.e. $MgCl_2(Mg(OR)_2)_2$.

Mechanical blend of amorphous $MgCl_2$ and $Mg(OR)_2$, wherein R is 2-ethylhexyl 1.0 g (3.537 mmol) of the produced $Mg(OR)_2$ was introduced into a 50 ml glass reactor. 168.6 mg (1.771 mmol) of the amorphous $MgCl_2$ was added on to this and the mixture was allowed to merge together during constant mixing. Both these mechanical blends were analysed in respect of their chemical composition and they were also characterised by means of their X-ray diffraction patterns.

Determination of Mg and Cl

The Mg containing complex samples were dissolved in a mixture of nitric and hydrofluoric acid and the metals were measured by flame atomic absorption with a nitrous oxide/acetylene flame. Chloride was determined after dissolution in dilute sulphuric acid by potentiometric titration with a standard silver nitrate solution.

GC-studies to measure alcohol content

To check the conversion rate of the 2-ethyl-hexanol (EHA) added in the synthesis the alcohol content of the mechanical blends were measured by gas chromatography (GC). This was done by first dissolving a 100 mg sample of the blend in 1 ml of n-pentanol. An internal alcohol standard (n-pentanol) was added. To improve the solubility of the sample in the solution the sample was kept in an ultrasound bath. To remove inorganic substances from the organic solution it was extracted with 1 ml of water and to ensure full dissolving another ml of the n-pentanol solution was added. To ensure repeatable equilibrium conditions between the organic layer and the water layer the samples were allowed to stand over night. The sample for the GC was taken from the alcohol layer. A Hewlett Packard 5890 GC with a 60 m DB-1 column was used for the GC analyses. The column had an diameter of 0.25 mm with a film thickness of 1 $\mu$m. An FID detector was used.

X-ray diffraction patterns

The WAXS patterns were collected in reflection mode between 2 and 70° 2Θ with a Siemens D500 instrument. The diffractometer was equipped with a Cu anode and a graphite monochromator in the reflected beam. The effect used was 40 kV and 35 mA. The sample was loaded in a glovebox into a Mylar film covered sample holder.

RESULTS AND DISCUSSION

Chemical composition of the mechanical blends

In Table 5 below the chemical composition of the achieved products are listed. In Table 5 is also shown the molar ratios between Mg, Cl and —OR, and these values are compared to the theoretically calculated values from the assumed molar composition of $MgCl_2(Mg(OR)_2)_2$. The experimentally found values showed that there was a 30% higher Cl content in the complexes than expected in both of the samples. The —OR % of sample A (using crystalline $MgCl_2$) was correspondingly smaller indicating a slightly higher proportion of the $MgCl_2$ component in this complex. The —OR % was of some reason higher in sample B (using amorphous $MgCl_2$).

TABLE 5

The chemical composition of the complexes compared to the theoretically calculated composition.

| Sample | Mg w-% | Cl w-% | EHA w-% | Mg | Cl | EHA |
|---|---|---|---|---|---|---|
| Calculated | 11.0 | 10.8 | 78.2 | 3 | 2 | 4 |
| A | 9.5 | 12.6 | 65.1 | 3 | 2.7 | 3.9 |
| B | 7.5 | 9.4 | 66.0 | 3 | 2.6 | 5.0 |

X-ray diffraction patterns of the mechanical blends

FIG. 8 shows the X-ray pattern for crystalline $MgCl_2$, FIG. 9 shows the pattern for amorphous $MgCl_2$, FIG. 10A shows the pattern for the mechanical blend of crystalline $MgCl_2$ and $Mg(OR)_2$ and FIG. 11 shows the pattern for the mechanical blend of amorphous $MgCl_2$ and $Mg(OR)_2$ (B). These X-ray patterns were compared to the X-ray pattern of the $MgCl_2$ enriched $Mg(OR)_2$ complex that was achieved in the above synthesis shown in FIG. 4. The results show that is just a mechanical blend between the two components as the different X-ray patterns for the crystalline $MgCl_2$ and for the $Mg(OR)_2$ can clearly be seen in the X-ray pattern of this sample. The pattern for sample B shows that in the mechanical blend of amorphous $MgCl_2$ and $Mg(OR)_2$ the later one is totally dominating covering under it to almost 100% the X-ray pattern of the amorphous $MgCl_2$. Both cases show that no new compound or complex is formed when just mechanically blending either chrystalline or amorphous $MgCl_2$ with $Mg(OR)_2$. The $MgCl_2$ $(Mg(OR)_2)_2$ complex formed trough the synthesis route described above gave a pattern showing a strong halo formation between 18° and 22° 2Θ, and in addition to this the strong signal at 7° 2Θ seen in all the $Mg(OR)_2$ patterns is totally lacking in the $MgCl_2$ $(Mg(OR)_2)_2$ complex patterns.

Just by mechanically mixing together $MgCl_2$ and $Mg(OR)_2$ in the correct proportion, the claimed complex was not formed. Both crystalline and amorphous $MgCl_2$ were tested. The results were interpreted by comparing the X-ray diffraction patterns of the complex formed. The results shows clearly that it was not possible to achieve a complex like $MgCl_2(Mg(OR)_2)_2$ just by mechanical blending, The X-ray studies showed that the result of the blending was a mixture of the original components: $MgCl_2$+ $Mg(OR)_2$.

Examples 8 to 11 (use of the complex for the preparation of an olefin polymerisation catalyst component)

Preparation of the olefin catalyst component 1.685 g (17.70 mmol) of anhydrous $MgCl_2$ was introduced in inert conditions into a 100 ml septum bottle. 11.12 ml (9.267 g, 70.80 mmol) of 2-ethyl-hexanol (EHA) was introduced on to the $MgCl_2$ and after this the temperature was increased to 125–128° C. to allow the reaction components to react with each other. After this, 8.81 ml (7.665 g, 83.19 mmol) of toluene was added after the reaction solution had cooled down to 110° C. After the addition of the toluene the reaction solution was cooled down to 21° C. Then 40 ml (29.160 g, 35.4 mmol) of a 20 w-% heptane solution of butyl-octyl-magnesium (BOMAG) was added. After this 5.10 ml (7.187 g, 35.4 mmol) of phthaloyl dichloride (PDC) was added to produce a $MgCl_2$ donor complex solution.

The $MgCl_2$ donor complex was now, drop by drop, added into 38.91 ml (67.159 g, 354 mmol) of $TiCl_4$ and allowed to react with this reagent at a temperature of 95° C. The reactants were allowed to react with each other for 30 min. After the $TiCl_4$ treatment, the complex was allowed to settle and the liquid was siphoned off. After this, 100 ml (86.6 g, 0.940 mol) of toluene was added on to the complex and the complex was washed in this solution at 90° C. for 20 min. Depending on which of the synthesis was under work, this washing step was done once (example 1), twice (example 2), three times (example 3) or four times (example 4). Finally, the catalyst complex was washed twice with 65 ml (44.44 g, 0.444 mol) portions of heptane for 20 min at 80° C. and thereafter, the complex was washed at room temperature with a 55 ml (34.44 g, 0.477 mol) portion of pentane for 20 min to improve the drying conditions. The catalysts were dried under a stream of nitrogen for one hour.

Results

Preparation of the complexes

The catalyst complexes achieved in this investigation are listed in Table 6.

TABLE 6

The catalyst complexes prepared in this test series.

| Example | Number of toluene washes | Colour of catalyst | Morphology of catalyst |
|---|---|---|---|
| 8 | 1 | Dark wine-red | Freely flowing |
| 9 | 2 | Dark wine-red | Freely flowing |
| 10 | 3 | Dark wine-red | Freely flowing |
| 11 | 4 | Dark wine-red | Freely flowing |

The chemical composition of the catalysts

The chemical composition of the catalysts were measured according to the description in the experimental section. In Table 7 the chemical composition of the catalysts are listed in w-% units and in Table 8 the chemical compositions are listed in mol-% units.

The chemical compositions of the catalysts were as expected on the basis of the reaction equation. With three washes a composition of $(MgCl_2)_6TiCl_4DOP$ was achieved. During the washes, there was a slightly higher wash out of $TiCl_4$ compared to DOP in the last catalyst. The amount of free alcohol (EHA) was also in this test series very low playing no significant part in the chemical composition (now 0.004–0.006 mol-%), i.e. being about 5% of the mol amount of $TiCl_4$ or DOP. The amount of phthalic anhydride was about 50% of the DOP amount. To sum up the results from the chemical measurements it can be said that the chemical composition of the catalyst complex when using the $MgCl_2$ enriched $Mg(OR')_2$ as a reagent in the catalyst synthesis is $(MgCl_2)_3TiCl_4DOP(PA)_{0.5}$.

TABLE 7

The chemical composition of the catalysts in w-% units

| Example | Mg w-% | Ti w-% | DOP w-% | EHA w-% | PA w-% |
|---|---|---|---|---|---|
| 8 | 7.8 | 4.7 | 33.6 | 0.72 | 6.7 |
| 9 | 8.1 | 4.7 | 32.0 | 0.54 | 7.4 |
| 10 | 10.2 | 3.2 | 28.5 | 0.58 | 6.5 |
| 11 | 12.9 | 1.6 | 21.6 | 0.51 | 6.1 |

TABLE 8

The chemical composition of the catalysts in mol-% units

| Example | Mg mol-% | Ti mol-% | DOP mol-% | EHA mol-% | PA mol-% |
|---|---|---|---|---|---|
| 8 | 0.321 | 0.098 | 0.086 | 0.0055 | 0.045 |
| 9 | 0.333 | 0.098 | 0.082 | 0.0041 | 0.050 |
| 10 | 0.420 | 0.067 | 0.073 | 0.0045 | 0.044 |
| 11 | 0.531 | 0.033 | 0.056 | 0.0039 | 0.041 |

CONCLUSIONS

In this work a $MgCl_2$ enriched Mg-alcoholate complex has been prepared. This was preferably done by pre-dissolving $MgCl_2$ into the alcohol used to prepare Mg-alcoholate from $MgR_2$. $MgCl_2 \cdot [Mg(OR)_2]_2$ was produced. This compound had a distinct halo in its X-ray diffraction patterns between 18°–22° 2Θ, resembling very much the halo that can be seen in diffraction patterns of calcinated silica. The diffraction pattern of this complex has its halo formation most probably from a reflection constellation of —Mg—OR—$MgCl_2$—OR—Mg—. The distinct halo formation in the $MgCl_2 \cdot [Mg(OR)_2]_2$ patterns separates this complex from the series of complexes consisting of $Mg(OR)_2$, $MgCl_2 \cdot 2ROH$, $MgCl_2 \cdot C_6H_4(COOR'')_2$ and $(MgCl_2)_2 \cdot TiCl_4 \cdot C_6H_4(COOR'')_2$ that all have a sharp distinct peak between 5° and 10° 2Θ. The Mg:Cl:OR ratio is improved in the $MgCl_2 \cdot [Mg(OR)_2]_2$ complex compared to the original $Mg(OR)_2$ compound from 1:0:2 to 3:2:4.

What is claimed is:

1. A complex product containing magnesium, halogen and alkoxy, characterised in that it has the following formula (1):

$$Mg_pX_q(OR)_{2p-q} \tag{1}$$

wherein X is a halogen, R is an alkyl group having from 1 to 20 carbon atoms, p is from 2 to 20, and $1 \leq q < p$.

2. A complex product according to claim 1, characterised in that X is chlorine.

3. A complex product according to claim 1 or 2, wherein R is an alkyl group having from 1 to 16 carbon atoms.

4. A complex product according to claim 1, wherein p is from 3 to 20.

5. A complex product according to claim 3, wherein R is an alkyl group having 4 to 12 carbon atoms.

6. A complex product according to claim 1, wherein said complex product is soluble in a non-polar solvent.

7. A complex product according to claim 6, characterized in that it has the formula (4):

$$MgCl_2 \cdot [Mg(OR)_2]_2$$

wherein R is an alkyl group having 1–16 carbon atoms.

8. A complex product according to claim 1, wherein it shows an X-ray diffraction pattern having a halo between 14° and 26° 2Θ.

9. A process for the preparation of a complex product according to claim 1, containing magnesium, halogen and alkoxy, wherein a magnesium dihalide, an alcohol having from 1 to 20 carbon atoms, and a dialkyl magnesium having from 2 to 40 carbon atoms are reacted to form said complex product.

10. A process according to claim 9, characterised in that said magnesium dihalide is magnesium dichloride.

11. A process according to claim 9 or 10, wherein said alcohol is a compound of the formula ROH wherein R is an alkyl having 1 to 20 carbon atoms.

12. A process according to claim 9, wherein said dialkyl magnesium is a compound of the formula $MgR'_2$, wherein each R' is the same or different and is an alkyl with 1 to 20 carbon atoms.

13. A process according to claim 9, comprising:
 a) reacting said magnesium dihalide and said alcohol to form an intermediate compound in liquid form, and
 b) reacting said intermediate compound in liquid form with said dialkyl magnesium to form said complex product.

14. A process according to claim 9, wherein said magnesium dihalide and said alcohol are reacted in a molar ratio of 1:2 to 1:8.

15. A process according to claim 9, said magnesium dihalide and said alcohol are reacted at 100 to 200° C.

16. A process according to claim 9, wherein magnesium dihalide and said alcohol are reacted for 1 to 8 hours.

17. A process according to claim 13, wherein a solvent is added to keep said intermediate in liquid form.

18. A process according to claim 17, wherein said magnesium dihalide and said solvent are used in a molar ratio of 1:4 to 1:100.

19. A process according to claim 9, wherein said magnesium dihalide and said dialkyl magnesium are used in a molar ratio of 1:1 to 1:4.

20. A process according to claim 9, wherein said dialkyl magnesium is provided in the form of a hydrocarbon solution having a molar ratio between said dialkyl magnesium and the hydrocarbon of said solution of 1:2 to 1:10.

21. A process according to claim 20, wherein the hydrocarbon of said hydrocarbon solution is a hydrocarbon having 5 to 12 carbon atoms.

22. A process according to claim 9, wherein said complex product is recovered in the form of a solution.

23. A method for preparing an olefin polymerization catalyst by contacting the complex according to claim 1 with titanium compound.

24. A complex product according to claim 3, wherein R is an alkyl group having 6 to 10 carbon atoms.

25. The method process according to claim 23, wherein said complex or a reaction product thereof, is in liquid form impregnated on a catalyst support.

26. The method according to claim 23, wherein said complex is in the form on an insoluble polymeric complex, acting as a Mg provider and catalyst support.

27. The method according to claim 23, wherein said catalyst support is an inert support.

28. The method according to claim 23, wherein said catalyst support is an inorganic inert support.

29. The method according to claim 28, wherein said inorganic inert support is selected from the group consisting of silica, alumina, a mixed oxide, and a mixture thereof.

30. The method according to claim 28, wherein said inorganic inert support is silica.

31. The process according to claim 21, wherein the hydrocarbon of said hydrocarbon solution is an aliphatic hydrocarbon having 6 to 10 carbon atoms.

32. The process according to claim 20, wherein said solution is a hydrocarbon solution having a molar ratio between said dialkyl magnesium and the hydrocarbon of said solution of 1:4 to 1:8.

33. The process according to claim 19, wherein the molar ratio between said magnesium dihalide and said dialkyl magnesium is 1:1 to 1:2.

34. The process according to claim 17, wherein said magnesium dihalide and said solvent are used in a molar ratio of 1:12 to 1:24.

35. The process according to claim 17, wherein said magnesium dihalide and said solvent are used in a molar ratio of 1:10 to 1:40.

36. The process according to claim 17, wherein said solvent is a hydrocarbon.

37. The process according to claim 17, wherein said solvent is an aromatic hydrocarbon.

38. The process according to claim 17, wherein said solvent is toluene.

39. The process according to claim 16, wherein said magnesium dihalide and said alcohol are reacted for 2 to 6 hours.

40. The process according to claim 15, wherein said magnesium dihalide and said alcohol are reacted at 110 to 150° C.

41. The process according to claim 14, wherein said magnesium dihalide and said alcohol are reacted in a molar ratio of 1:3 to 1:5.

42. The process according to claim 14, wherein said magnesium dihalide and said alcohol are reacted in a molar ratio of 1:4.

43. The process according to claim 12, wherein each R' is the same or different and is an alkyl with 2 to 12 carbon atoms.

44. The process according to claim 12, wherein each R' is the same or different and is an alkyl with 4 to 10 carbon atoms.

45. The process according to claim 11, wherein R is an alkyl having 4 to 12 carbon atoms.

46. The process according to claim 11, wherein R is an alkyl having 6 to 10 carbon atoms.

47. The complex product according to claim 7, wherein R is an alkyl group having 4 to 12 carbons.

48. The complex product according to claim 7, wherein R is an alkyl group having 6 to 10 carbon atoms.

49. The complex product according to claim 6, wherein said complex product is soluble in a hydrocarbon.

50. The complex product according to claim 6, wherein said complex product is soluble in an aromatic hydrocarbon.

51. The complex product according to claim 6, wherein said complex product is soluble in toluene.

52. The complex product according to claim 4, wherein p is from 3 to 10.

53. The complex product according to claim 4, wherein p is from 3 to 6.

54. The complex product according to claim 4, wherein p is from 3 to 4.

55. The complex product according to claim 4, wherein p is 3.

* * * * *